United States Patent [19]

Elder et al.

[11] Patent Number: 5,155,080

[45] Date of Patent: * Oct. 13, 1992

[54] PROCESS AND CATALYST FOR PRODUCING SYNDIOTACTIC POLYOLEFINS

[75] Inventors: Michael J. Elder, Friendswood, Tex.; Abbas Razavi, Colfontaine, Belgium; John A. Ewen, Houston, Tex.

[73] Assignee: Fina Technology, Inc., Dallas, Tex.

[*] Notice: The portion of the term of this patent subsequent to Jan. 9, 2007 has been disclaimed.

[21] Appl. No.: 419,055

[22] Filed: Oct. 10, 1989

Related U.S. Application Data

[63] Continuation-in-part of Ser. No. 220,007, Jul. 15, 1988, Pat. No. 4,852,851.

[51] Int. Cl.$^5$ ................................ C08F 4/64
[52] U.S. Cl. ........................... 502/152; 502/103; 502/117; 526/170
[58] Field of Search ............... 502/103, 117, 152

[56] References Cited

U.S. PATENT DOCUMENTS

| | | | |
|---|---|---|---|
| 3,135,809 | 6/1964 | Bosmasian | 502/103 X |
| 3,258,455 | 6/1966 | Natta et al. | 260/93.7 |
| 3,305,538 | 2/1967 | Natta et al. | 260/93.7 |
| 3,364,180 | 1/1968 | Emrick | 260/93.7 |
| 4,794,096 | 12/1988 | Ewen | 502/117 |
| 4,892,851 | 1/1990 | Ewen et al. | 502/103 X |

FOREIGN PATENT DOCUMENTS 277003  8/1988  European Pat. Off. .
277004  8/1988  European Pat. Off. .

OTHER PUBLICATIONS

Zambelli et al., Macromolecules, 1989, pp. 2186-2189.
Jordan et al., (1), JACS (1986), 108, pp. 7410-7411.
Jordan et al., (2), JACS (1986), 108, pp. 1718-1719.

*Primary Examiner*—Patrick P. Garvin
*Attorney, Agent, or Firm*—William D. Jackson; Jim D. Wheelington

[57] ABSTRACT

Syndiospecific catalysts and processes for the syndiotactic propagation of a polymer chain derived from an ethylenically unsaturated monomer which contains 3 or more carbon atoms or is a substituted vinyl compound. The catalysts comprise an unbalanced metallocene cation, characterized by a cationic metallocene ligand having sterically dissimilar ring structures joined to a positively charged coordinating transition metal atom, and a stable noncoordinating counter anion for the metallocene cation. One of said ring structures is a substituted or unsubstituted cyclopentadienyl ring and the other of the ring structures is a substituted cyclopentadienyl group which is sterically different from the first cyclopentadienyl group. A structural bridge between cyclopentadienyl groups imparts stereorigidity to the catalyst. The catalyst is contacted with a $C_3+$ alpha olefin or other ethylenically unsaturated compound in a polymerization reaction zone and maintained in contact with the catalyst in the reaction zone under polymerizatio conditions to produce a syndiotactic polymer.

8 Claims, No Drawings

PROCESS AND CATALYST FOR PRODUCING SYNDIOTACTIC POLYOLEFINS

This application is a continuation in part of application Ser. No. 220,007 filed Jul. 15, 1988, and now U.S. Pat. No. 4,892,851.

TECHNICAL FIELD

This invention relates to processes for the production of syndiotactic polymers and more particularly to the production of a syndiotactic polyolefin by polymerization of propylene or higher alpha olefin over a stereorigid cationic metallocene catalyst having dissimilar cyclopentadienyl rings.

BACKGROUND OF THE INVENTION

Syndiotactic polymers have a unique stereochemical structure in which monomeric units having enantiomorphic configuration of the asymmetrical carbon atoms follow each other alternately and regularly in the main polymer chain. Syndiotactic polypropylene was first disclosed by Natta et al. in U.S. Pat. No. 3,258,455. As disclosed in this patent, syndiotactic polypropylene is produced by using a catalyst prepared from titanium trichloride and diethyl aluminum monochloride. A later patent to Natta et al., U.S. Pat. No. 3,305,538, discloses the use of vanadium triacetylacetonate or halogenated vanadium compounds in combination with organic aluminum compounds for producing syndiotactic polypropylene. U.S. Pat. No. 3,364,190 to Emrick discloses a catalyst system composed of finely divided titanium or vanadium trichloride, aluminum chloride, a trialkyl aluminum and a phosphorus containing Lewis base as producing syndiotactic polypropylene. As disclosed in these patent references and as known in the art, the structure and properties of syndiotactic polypropylene differ significantly from those of isotactic polypropylene. The isotactic structure is typically described as having the methyl groups attached to the tertiary carbon atoms of successive monomeric units on the same side of a hypothetical plane through the main chain of the polymer, e.g., the methyl groups are all above or below the plane. Using the Fischer projection formula, the stereochemical sequence of isotactic polypropylene is described as follows:

Another way of describing the structure is through the use of NMR. Bovey's NMR nomenclature for an isotactic pentad is ... mmmm ... with each "m" representing a "meso" dyad or successive methyl groups on the same side in the plane. As known in the art, any deviation or inversion in the structure of the chain lowers the degree of isotacticity and crystallinity of the polymer.

In contrast to the isotactic structure syndiotactic polymers are those in which the methyl groups attached to the tertiary carbon atoms of successive monomeric units in the chain lie on alternate sides of the plane of the polymer. Syndiotactic polypropylene is shown in zig-zag representation as follows:

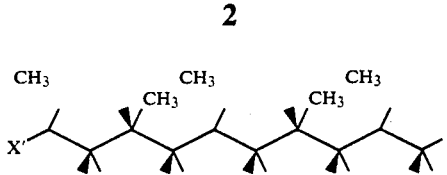

Corresponding representations for syndiotactic polyvinylchloride and polystyrene respectively are:

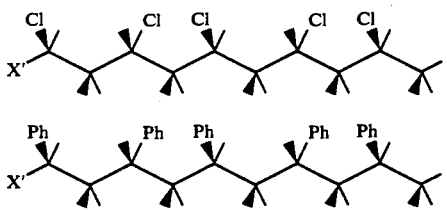

Using the Fischer projection formula, the structure of a syndiotactic polymer is designated as:

In NMR nomenclature, this pentad is described as ... rrrr ... in which each "r" represents a "racemic" dyad, i.e., successive methyl groups on alternate sides of the plane. The percentage of r dyads in the chain determines the degree of syndiotacticity of the polymer. Syndiotactic polymers are crystalline and, like the isotactic polymers, are insoluble in xylene. This crystallinity distinguishes both syndiotactic and isotactic polymers from an atactic polymer that is soluble in xylene. An atactic polymer exhibits no regular order of repeating unit configurations in the polymer chain and forms essentially a waxy product.

While it is possible for a catalyst to produce all three types of polymers, it is desirable for a catalyst to produce predominantly isotactic or syndiotactic polymer with very little atactic polymer. Catalysts that produce isotactic polyolefins are disclosed in copending U.S. patent application Ser. Nos. 034,472 filed Apr. 3, 1987 and now abandoned; 096,075 filed Sep. 11, 1987 (now U.S. Pat. No. 4,794,096); and 095,755 filed on Sep. 11, 1987 and now abandoned. These applications disclose chiral, stereorigid metallocene catalysts that polymerize olefins to form isotactic polymers and are especially useful in the polymerization of a highly isotactic polypropylene.

Catalysts that produce syndiotactic polypropylene or other syndiotactic polyolefins are disclosed in the aforementioned application Ser. No. 220,007 (now U.S. Pat. No. 4,892,851). These catalysts are bridged stereorigid metallocene catalysts. The catalysts have a structural bridge extending between dissimilar cyclopentadienyl groups and may be characterized by the formula:

$$R''(CpR_n)(CpR'_m)MeQ_k \qquad (1)$$

In formula (1), Cp represents a cyclopentadienyl or substituted cyclopentadienyl ring; and R and R' represent hydrocarbyl radicals having 1–20 carbon atoms R'' is a structural bridge between the rings imparting stereorigidity to the catalyst; Me represents a transition metal and Q a hydrocarbyl radical or halogen. $R'_m$ is selected so that (CpR'$_m$) is a sterically different substituted cyclopentadienyl ring than (CpR$_n$). n varies from 0 to 4 (0 designating no hydrocarbyl groups, i.e. an unsubstituted cyclopentadienyl ring), m varies from 1-4, and K is from 0-3. The sterically different cyclopentadienyl rings produce a predominantly syndiotactic polymer rather than an isotactic polymer. Metallocene catalysts of yet another type are cationic catalysts as disclosed in European Patent Applications 277,003 to Turner et al. and 277,004 to Turner. As disclosed in these applications, a bis(cyclopentadienyl) zirconium, titanium or hafnium compound is reacted with a second compound comprising a cation capable of donating a proton or an ion exchange compound comprising a cation which will irreversible react with a ligand on the first compound, and a bulky, stable anion. The catalysts described in the European Patent Applications 277,003 and 277,004 are disclosed as especially useful in the polymerization of ethylene and more generally in the polymerization of alpha olefins, diolefins and/or an acetylenically unsaturated compounds containing from 2-18 carbon atoms. Principally disclosed in the European applications is the polymerization of ethylene or the copolymerization of ethylene with propylene or 1 butene or with propylene and 1- butene or 1,4 hexadiene. Stereospecificity, or lack thereof, of the polymers as disclosed in the Turner and Turner et al. applications are not generally discussed, although in application Ser. No. 277,004 examples are given of producing atactic polypropylene and in one instance (Example 39) isotactic polypropylene.

SUMMARY OF THE INVENTION

In accordance with the present invention, there are provided syndiospecific catalysts and processes for the syndiotactic propagation of a polymer chain derived from an ethylonically unsaturated monomer which contains 3 or more carbon atoms or is a substituted vinyl compound. Syndiospecific propogation of the polymer chain is carried out in the presence of a stereorigid cationic metallocene catalyst which incorporates dissimilar cyclopentadienyl rings at least one of which is substituted and both of which are in a stereorigid relationship relative to the coordinating metal atom of the metallocene complex. The catalyst is contacted with the catalyst in the reaction zone under polymerization conditions to produce a syndiotactic polymer. The preferred application of the invention is in the production of syndiotactic polypropylene. Catalysts in accordance with the present invention may be characterized by formula (2) as follows:

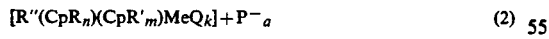

[R"(CpR$_n$)(CpR'$_m$)MeQ$_k$]+P$^-$$_a$ (2)

Wherein:
Cp is a cyclopentadienyl or a substituted cyclopentadienyl ring; each R and R' is the same or different and is a hydrocarbyl radical having from 1-20 carbon atoms and selected such that CpR'$_m$ is a sterically different ring than CpRn.
R" is a structural bridge between the Cp rings imparting stereorigidity to the catalyst;
Me is a Group 4, 5, or 6 metal from the Periodic Table of Elements;
n is from 0 to 4; m is from 1 to 4; and K is from 0 to 2;
P$_a$ is a stable noncoordinating anion.

DETAILED DESCRIPTION

The present invention involves the use of certain stereorigid cationic metallocenes as catalysts in syndiotactic polymer propogation. The term metallocene as used herein and in accordance with normal art usage denotes an organometallic coordination compound in which two cyclo C5 ligands (cyclopentadienyl or substituted cyclopentadienyl rings) are bonded to a central or "sandwiched" metal atom which may be provided by a transition metal or metal halide, alkyl, alkoxy, or alkyl or alkoxy halide or the like. Such structures are sometimes referred to as "molecular sandwiches" since the cyclo-C$_5$ ligands are oriented above or below the plane of the central coordinated metal atom. By the term "cationic metallocene" is meant a metallocene in which the central coordinated metal atom carries a positive charge, that is, the metallocene complex is a cation associated with a stable anion. The cationic metallocenes used in the present invention are stereorigid. Stereorigidity is imparted to the metallocene complex to prevent rotation of the cyclopentadienyl or substituted cyclopentadienyl rings about their coordination axes by a chemical bridge extending between the cyclopentadienyl (or substituted cyclopentadienyl) rings.

As noted previously, U.S. Pat. No. 4,892,851 discloses the preparation of syndiotactic polypropylene, or other polyolefins, through the use of stereorigid metallocene catalysts. While the metallocenes in U.S. Pat. No. 4,892,851 may be neutral, the present invention employs stereorigid metallocene catalysts, which may be of the type in which stereorigidity is imparted by a bridge structure as disclosed in U.S. Pat. No. 4,892,851, in which the metallocene ligand is ionized to provide a stable cationic catalyst. The cationic metallocene catalyst employed in the present invention may be prepared following procedures of the type disclosed in the aforementioned European Applications 277,003 and 277,004, but they preferably are prepared by a process employing a triphenylcarbenium borate as discussed in greater detail below. Where procedures of the type disclosed in the Turner and Turner et al. European applications are used in the preparation of cationic metallocene catalysts to be employed in the present invention certain important distinctions must be observed as evidenced by the fact that neither of the European applications disclose the preparation of syndiotactic polymers. Thus, in the metallocene catalyst disclosed in the Turner European applications the cyclopentaldienyl groups may be the same or different, and while they can be bridged, they need not be and, in fact, are usually unbridged. Moreover, to the extent that the metallocene catalysts disclosed in the European applications are bridged to impart stereorigidity, they are also, symetrical. In contrast to the teachings of the Turner European applications, the cationic metallocene catalysts employed in the present invention must not only be stereorigid, the cyclopentadienyl groups must be dissimilar.

Stereorigid cationic metallocene catalysts employed in the present invention may be characterized by the following formulas:

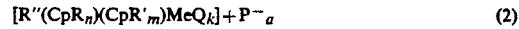

[R"(CpR$_n$)(CpR'$_m$)MeQ$_k$]+P$^-$$_a$ (2)

wherein: Cp, R, R', R", Me, Q, P$_a$, k, m, and n are as described previously. Stereorigidity is imparted by means of a structural bridge similarly as described in the parent application Ser. No. 220,007.

The anion indicated by P in formula (2) is a compatible noncoordinating anion which may be of the type described in the aforementioned Turner European applications. The anion P either does not coordinate with the metallocene cation or is only weakly coordinated to the cation thereby remaining sufficiently labile to be displaced by a neutral Lewis base. As described in the Turner applications, the term "compatible noncoordinating anion" identifies an anion which when functioning as a stabilizing anion in the metallocene catalyst system does not transfer an anionic substituent or fragment thereof to the cation to form a neutral metallocene and boron byproduct or other neutral metal or metaloid byproduct, as the case may be. Suitable noncoordinating anions include $[W(PhF_5)]^-$, $[Mo(PhF_5)]^-$ (wherein $PhF_5$ is pentafluorophenyl), $[ClO_4]^-$, $[S_2O_6]^-$, $[PF_6]^-$, $[SbR_6]^-$, $[AlR_4]^-$ (wherein each R is independently, Cl, a $C_1$-$C_5$ alky group preferably a methyl group, an aryl group, e.g. a phenyl or substituted phenyl group, or a fluorinated aryl group.) For a further description of compatible noncoordinating anions and their associated cations which may be employed in the present invention, reference is made to European applications 277,003 and 277,004, the entire disclosures of which are incorporated herein by reference. In considering these disclosures, it must be recalled, however, that unlike the cationic metallocene catalyst of the Turner European applications, the cationic metallocene catalyst employed in the present invention must be stereorigid with dissimilar Cp rings. The size of the counter ion will also depend on the bulk of the substituent groups on the cyclopentadienyl rings. Monomer insertion and isomerization is controlled primarily by the relationship of the counterion to the bridged structure.

In addition to size, the other important characteristics of the anionic counterions are stability and bonding. The anion must be sufficiently stable so that it cannot be rendered neutral by virtue of the metallocene cation extracting an electron. The bond strength with the cation is, such that it makes way for the inserting monomer in the chain growing reaction.

The metallocene catalysts disclosed in the Turner European applications suffer from certain disadvantages in that Lewis bases may be produced by protonation of the metallocene ligand which function as poisons for the metallocene catalyst. The result may be a catalyst which is inactive. A preferred procedure for producing cationic metallacene catalyst of the type employed in the present invention involves the reaction of an ionic compound in a noncoordinating solvent with a dimethyl metallocene which is unbalanced and stereorigid by virtue of a bridge between the cyclopentadienyl groups. By way of example, triphenylcarbenium tetrakis(pentafluorophenyl) boronate may be reacted with the neutral metallocene in a solvent such as toluene. Such catalysts and their preparation are disclosed in U.S. patent application Ser. No. 419,046 by John A. Ewen and Michael J. Elder for "Preparation of Metallocene Catalysts for Polymerization of Olefins" filed on even date herewith, and now abandoned, the entire disclosure of which is incorporated by reference.

A preferred application of the invention is in the syndiotactic polymerization of C3+ alpha olefins, specifically propylene, but the invention may be employed in the preparation of other polymers from ethylenically unsaturated monomers where syndiotacticity is a desired structure. For example, syndiospecific propagation of a polymer chain from 1 butene may be carried out in accordance with the invention. By the term ethylenically unsaturated monomer as used herein is meant a hydrocarbon or substituted hydrocarbon compound characterized by a terminal vinyl group ($CH_2=CH-$). Such compounds as may be employed in the present invention have at least three carbon atoms or are a substituted vinyl compound, specifically vinyl chloride. They may be characterized in terms of the following formula:

$$CH_2=CH-R$$

wherein: R is a hydrocarbyl group or nonhydrocarbyl substituent. Specific polymers in which syndiotacticity is sometimes desirable and to which the invention is applicable include polyvinyl chloride and polystyrene. The polymerization of a 1-diene such as 1,3-butadiene may also be carried out in accordance with the present invention to achieve a syndiotactic polymer configuration. Syndiotactic polypropylene is probably of the greatest practical significance and the invention will be described in detail with reference to the production of syndiotactic polypropylene. However, other compounds in which the syndiotactic configuration is desirable are also of interest.

Polymerization procedures as disclosed in the aforementioned parent application Ser. No. 220,007 may be employed in carrying out the present invention. Co-catalysts, usually organo-aluminum compounds such as trialkylaluminum, trialkyloxyaluminum, dialkylaluminum halides or alkylaluminum dihalides may be employed in the present invention. Especially suitable alkylaluminums are trimethylaluminum and triethylaluminum with the latter, commonly referred to as TEAL, being most preferred. However, methylaluminoxane (MAO) which may be used as a co-catalyst in the parent application Ser. No. 220,007 (now U.S. Pat. No. 4,892,851) need not be, and preferably is not, used in carrying out the present invention. While applicant's invention is not to be restricted by theory, it is believed that neutral metallocenes of the type disclosed in the parent application form cationic complexes by reaction with the MAO in the manner as disclosed by Zambelli, A. et al., "Isotactic Polymerization of Propene: Homogenous Catalysts Based on Group 4 Metallocenes Without Methylalumoxane", Macro-Molecules 1989, 22, pages 2186-2189. It is believed that the anionic species derived from the MAO compound may function to influence monomer insertion to cause isomerization which when coupled with the chain migration from one catalyst site to the other during the growth of the polymer chain results in syndiotacity. The stereorigid cationic metallocene catalysts employed in the present invention accomplish isomerization during monomer insertion and chain migration.

The procedures and reaction conditions disclosed in the aforementioned patent application Ser. No. 220,007 (now U.S. Pat. No. 4,892,851) may be employed in the present invention with the exception, as noted above, that MAO need not be used and preferably is not used. The prior art discloses the use of MAO as a co-catalyst with metallocene catalysts in amounts well in excess of the stoichiometric equivalent amount providing mole ratios of aluminum to the coordinating metal (Me) of about 100-1000. MAO usually is not employed in the present invention and if it is used it is in amounts well below the aforementioned range and preferably providing an Al/Me mole ratio of no more than 10 and, more preferably, no more than 1.

The catalysts used in the present invention are syndio-specific and produce a polymer with a high syndiotactic index. As disclosed in U.S. Pat. No. 4,892,851, syndiotactic polymers generally have lower heats of crystallization than the corresponding isotactic polymers. In addition, for the same number of imperfections in the polymer chain, syndiotactic polymers have a higher melting point than isotactic polymers.

The metallocene catalysts used in the present invention may be bridged structures substantially the same as disclosed in U.S. Pat. No. 4,892,851 but must be cationic in form, and for a further description of such bridged metallocenes the entire disclosure of U.S. Pat. No. 4,892,851 is incorporated herein by reference. The R" structural bridge is preferably selected from the group consisting of alkyl radicals having 1-6 carbon atoms, more preferably 1-4, or a hydrocarbyl radical containing silicon, germanium, phosphorus, nitrogen, boron, or aluminum. Alkyl bridges are preferred. Examples include methyl, ethyl and propyl bridges which may be substituted or unsubstituted. Me is a Group 4, 5, or 6 metal from the Periodic Table of Elements but preferably is a Group 4 or 5 metal and more preferably a Group 4 metal, specifically titanium, zirconium or hafnium. Vanadium is the most suitable of the Group 5 metals; each Q is a hydrocarbyl radical having 1-20 carbon atoms or is a halogen. As a practical matter, Q will usually be a methyl or ethyl group or chlorine. In order to be syndio-specific, the Cp rings in the metallocene catalysts must be substituted in a substantially different manner so that there is a steric difference between the two Cp rings, and therefore, R'm is selected such that (CpR'$_m$) is a substantially different substituted ring than (CpR$_n$). In order to produce a syndiotactic polymer, the characteristics of the groups substituted directly on the cyclopentadienyl rings seem to be important. Thus, by "steric difference" or "sterically different" as used herein, it is intended to imply a difference between the steric characteristics of the Cp rings that controls the approach of each successive monomer unit that is added to the polymer chain. The steric difference between the Cp rings acts to block the approaching monomer from a random approach and controls the approach such that the monomer is added to the polymer chain in the syndiotactic configuration.

Preferably, the syndiospecific metallocene catalysts of the present invention exhibit bilateral symmetry of the metallocene ligands when viewed as planar projections of the cyclopentadienyl groups. By the term "bilateral symmetry" as used here, is meant the symmetry of the ligand as viewed through the axes of the substituted or unsubstituted Cp groups. For example, the isopropylidene (cyclopentadienyl-1-fluorenyl) ligand would exhibit such bilateral symmetry whereas the corresponding structure but with the cyclopentadienyl group substituted at the three position would not exhibit bilateral symmetry. The ligand with two identical substituents at the 3 and 4 position on the cyclopentadienyl group would have bilateral symmetry.

Without intending to limit the scope of the present invention as indicated by the claims, it is believed that in the polymerization reaction both the catalyst and the approaching monomer units isomerize with each monomer addition to the polymer chain as the chain migrates between catalyst sites. This isomerization of the monomer which is controlled by the steric blockage of the differently substituted Cp rings results in the alternating configuration characteristic of syndiotactic polymers and is in contrast to the chain-end control of the catalysts disclosed by Natta et al. The different reaction mechanism also results in a different structure for the polymer.

In the preferred catalysts for use in the present invention, Me is titanium, zirconium or hafnium; Q is preferably a methyl or halogen, preferably chlorine; and k is preferably 1, but it may vary with the valence of the metal atom. Exemplary hydrocarbyl radicals include methyl, ethyl, propyl, isopropyl, butyl, isobutyl, amyl, isoamyl, hexyl, heptyl, octyl, nonyl, decyl, cetyl, phenyl, and the like. Other hydrocarbyl radicals useful in the present catalysts include other alkyl, aryl, alkenyl, alkylaryl or arylalkyl radicals. Further, Rn and R'm may comprise hydrocarbyl radicals attached to a single carbon atom in the Cp ring as well as radicals that are bonded to two carbon atoms in the ring. The catalysts used in the present invention may be prepared by converting a neutral metallocene moiety prepared in accordance with procedures such as disclosed in U.S. Pat. No. 4,892,851 and which is then converted to the cationic state, following procedures such as disclosed in the aforementioned European applications 277,003 and 277,004 or more preferably by reaction with triphenylcarbenium boronates as described in the aforementioned copending application Ser. No. 419,046, now abandoned. Suitable metallocene precursors (prior to reaction to form the cationic catalysts) are methylene(cyclopentadienyl-1-fluorenyl)zirconium dimethyl, ethylene(cyclopentadienyl-1-fluorenyl)zirconium dimethyl and methylene(indenyl)(cyclopentadienyl)zirconium dimethyl, isopropylidene(cyclopentadienyl-1-fluorenyl) zirconium dimethyl and the corresponding dichlorides.

The Examples below disclose methods of preparing the catalyst precursors with the second method being preferred as it produces a more stable and active catalyst. It is important that the catalyst complex be "clean" as usually low molecular weight, amorphous polymer is produced by impure catalysts. Generally, the preparation of the metallocene complex consists of forming and isolating the Cp or substituted Cp ligands which are then reacted with a halogenated metal to form the complex.

The examples given below illustrate the preparation of neutral metallocenes which may then be converted to cationic metallocene catalysts for use in the invention. Three different synthesis procedures, designated as A, B and C, are described for both zirconium and hafnium metallocene catalysts. The synthesis procedures in all methods were performed under an inert gas atmosphere using a Vacuum Atmospheres glovebox or Schlenk techniques. The synthesis process generally comprises the steps of 1) preparing the halogenated or alkylated metal compound, 2) preparing the ligand, 3) synthesizing the complex, and 4) purifying the complex. The synthesis of the bridged, substituted dicyclopentadienyl ligand was accomplished by contacting a substituted fulvene with a substituted cyclopentadienyl under reaction conditions sufficient to produce a bridged structure having the requisite dissimilar cyclopentadienyl rings. In fulvene, a terminal carbon atom is bound by a double bond to a cyclopentadienyl ring as indicated by the formula Cp=CH$_2$.

$$Cp=CH_2 \tag{3}$$

In substituted fulvene, the terminal carbon atom is disubstituted and substituent groups may also occur on the Cp ring in accordance with the following formula:

(4)

In formula (4) R and R' are hydrocarbyl radicals, with each R and R' being the same or different, and $0 < a < 4$. The other three steps of the synthesis may be performed as shown below or by other methods known in the art. The catalyst precursor produced by these methods from dimethylfulvene and fluorene is isopropylidene (cyclopentadienyl-1-fluorenyl) $MeCl_2$ wherein Me is either zirconium or hafnium depending on the example.

In Method A, the halogenated metal compound was prepared using tetrahydrofuran ("THF") as a solvent resulting in THF bound in with the final catalyst complex. Specifically, $MeCl_4.2THF$ was prepared as described in Manzer, L., Inorg. Synth., 21, 135–36 (1982). In the Examples below, Me is zirconium and hafnium, but it may also include titanium or other transition metals.

The substituted dicyclopentadienyl ligand may be prepared using various processes known in the art depending upon the selection of the specific bridge or ring substituents. In the preferred embodiments shown in the Examples below, the ligand is 2,2-isopropylidene (cyclopentadienyl-1-fluorenyl). To prepare this ligand, 44 gms (0.25 mol) of fluorene were dissolved in 350 ml THF in a round bottom flask equipped with a side arm and dropping funnel. Contained within the funnel were 0.25 mol of methyl lithium ($CH_3Li$) in ether (1.4M). The $CH_3Li$ was added dropwise to the fluorene solution and the deep orange-red solution was stirred for several hours. After gas evolution had ceased, the solution was cooled to $-78°$ C. and 100 ml of THF containing 26.5 gms (0.25 mol) of 6,6- dimethylfulvene was added dropwise to the solution. The red solution was gradually warmed to room temperature and stirred overnight. The solution was treated with 200 ml of water and stirred for ten minutes. The organic fraction of the solution was extracted several times with 100 ml portions of diethylether, and the combined organic phases were dried over magnesium sulfate. Removal of the ether from the organic phases left a yellow solid which was dissolved in 500 ml of chloroform and recrystallized by addition of excess methanol at $2°$ C. to yield a white powder.

The elemental analysis of the ligand showed carbon to be 91.8% by weight of the compound and hydrogen to be 7.4% by weight. This corresponds to the weight percentages for $C_{21}H_{20}$, 92.6% carbon and 7.4% hydrogen. The NMR spectrum for the ligand establishes the structure to include one cyclopentadienyl ring attached by an isopropyl bridge to a second cyclopentadienyl ring that is substituted to form a fluorenyl radical.

A neutral metallocene complex was synthesized using this ligand and the metal tetrachloride-THF complex. The catalyst was formed by adding 0.05 mol of n-butyl lithium hexane (1.6M) dropwise to a 100 ml THF solution containing 6.8 gms (0.025 mol) of the Cp ligand described above. The solution was stirred at $35°$ C. for twelve hours after which 9.4 gms (0.025 mol) of $ZrCl_4.2THF$ contained in 200 ml of THF were rapidly cannulated together with the ligand solution into a 500 ml round bottom flask with vigorous stirring. The deep orange-red solution was stirred for twelve hours under reflux. A mixture of LiCl and a red solid were isolated by removing the solvents under vacuum.

Metallocene complexes produced in accordance with Method A are noted to be somewhat impure and extremely air and moisture sensitive. As a result, in the Examples below, Method A catalysts were purified using one or more of the following purification procedures:

1. Extraction with pentane. Trace quantities of a yellow impurity contained in the solid red catalyst complex were repeatedly extracted with pentane until the pentane became colorless.

2. Fractional recrystallization. The red complex was separated from the white LiCl by dissolving it in 100 ml of toluene, filtering it through a fine porosity sintered glass frit, and forming a saturated solution by adding pentane. The red zirconium complex was isolated using crystallization at $-200°$ C.

3. Chromotography on Bio-Beads. 50 gms of Bio-Beads SM-2 (20–50 mesh spherical, macroreticular styrene-divinylbenzene copolymer from Bio-Rad laboratories) were dried under vacuum at $70°$ C. for 48 hours in a $30 \times 1.5$ centimeter column. The beads were then equilibrated with toluene for several hours. A concentrated solution of the red catalyst complex in toluene was eluted down the column with 150–200 ml of toluene. The complex was recovered by evaporating the toluene under vacuum.

As an alternative synthesis procedure, Method B provides neutral metallocenes that are more air stable, more active, and which can be converted to cationic catalysts producing a higher percentage of syndiotactic polypropylene. In this process, methylene chloride is used as a non-coordinating solvent. The process described below uses hafnium as the transition metal, but the procedure is adaptable for use with zirconium, titanium or other transition metals. The substituted dicyclopentadienyl ligand was synthesized in THF in the same manner as described in Method A above. The red dilithio salt of the ligand (0.025 mol) was isolated as disclosed in Method A by removing the solvents under vacuum and by washing with pentane. The isolated red dilithio salt was dissolved in 125 ml of cold methylene chloride and an equivalent amount (0.025 mol) of $HfCl_4$ was separately slurried in 125 ml of methylene chloride at $-78°$ C. The $HfCl_4$ slurry was rapidly cannulated into the flask containing the ligand solution. The mixture was stirred for two hours at $-78°$ C., allowed to warm slowly to $25°$ C. and stirred for an additional 12 hours. An insoluble white salt (LiCl) was filtered off. A moderately air sensitive, yellow powder was obtained by cooling the brown/yellow methylene chloride solution to $-20°$ C. for 12 hours and cannulating away the supernatant. The bright yellow product was washed on the sintered glass filter by repeatedly filtering off cold supernatant that had been cannulated back over it. The catalyst complex was isolated by pumping off the solvents using a vacuum, and it was stored under dry, deoxygenated argon. The process yielded 5.5 gms of catalyst complex.

The elemental analysis of the hafnium complex prepared using Method B showed that the metallocene consisted of 48.79% by weight of carbon, 3.4% hydrogen, 15.14% chlorine and 33.2% hafnium. These percentages compare with the theoretical analysis for $C_{21}H_{18}HfCl_2$ which is 48.39% carbon, 3.45% hydrogen, 13.59% chlorine and 34.11% hafnium. Similarly, zirconium catalysts produced using Method B show elemental analysis close to the expected or theoretical values. Further, some of the hafnium complexes illustrated in the Examples below were made using 96% pure $HfCl_4$ which also contains about 4% $ZrCl_4$. Still other catalyst samples were made using 99.99% pure $HfCl_4$. Differences can be seen in the molecular weight distributions of the polymers produced with the pure Hf catalyst in neutral form compared with polymers produced using the catalysts which contain a small percentage of zirconium. In view of this, the cationic mixed catalyst can be expected to produce a polymer with a broader molecular weight distribution than that produced by a pure catalyst system.

For Method C, 5.00 grams (0.018M) of the substituted cyclopentadienyl ligand was dissolved under inert atmosphere in 60 mL of distilled THF. After cooling to 0° C. for 10 minutes, 18 mL of 2.5M n-butyllithium solution (in hexane; 0.044M) was added dropwise over 1 hour. The resultant pink solution was warmed to room temperature and stirred for a combined total of 2 hours. Removing the solvent on a vacuum line gave a pink solid of the dilithio salt, which was washed three times with 150 mL of dry, degassed pentane. The orange-yellow solid that remained was vacuum dried for 2 hours, redissolved at room temperature in 50 mL distilled toluene and the red solution cooled to $-77°$ C. The reaction flash was armed to room temperature and stirred for 14 hours. A slurry of 4.2 grams of $ZrCl_4$ (0.018M) in 50 mL toluene was added; another 100 mL of toluene in 4 portions was used to wash all of the $ZrCl_4$ into the reaction flask. After stirring for 1 hour at $-77°$ C. Removal of the solvent via double-ended needle gave a clear red filtrate with a white gummy residue on the filter. Removing the solvent from the filtrate gave a red powder (4.91 g, 0.011M, 62%) which was vacuum dried and stored under dry, deoxygenated argon.

The complex was recrystallized by dissolving in a minimum volume of distilled $CH_2Cl_2$ and filtering through a fine frit. Addition of an equal volume of hexane and concentration of the bright red solution of $-77°$ C. gave red crystals, which were collected by cannulating off the solvent and vacuum drying.

Two alternative procedures were employed in synthesis of iPr[Cp-1-Flu]Zr(CH$_3$)$_2$. In the first procedure 2 g of iPr[Cp-1-Flu]ZrCl$_2$ as prepared in Method B above were suspended in 100 ml of diethyl ether contained in a round bottom flask which was equipped with a side arm, a dropping funnel and a magnetic stirring bar. The suspension was cooled to $-70°$ C. 2 equivalents of methyl magnesium chloride (3.1 ml, 3M solution in THF were added dropwise. The cold bath was removed and the flask warmed to room temperature. A bright yellow ether solution was obtained after filtering off the magnesium chloride. The ether was evaporated, and the yellow solid was redissolved in 50 ml of warm toluene. Addition of 50 ml pentane and cooling to $-20°$ C. resulted in 1.75 g of the yellow complex (94% yield).

In the second procedure, 28 mmol methylmagnesium chloride (3.0M solution in THF) was added dropwise to a slurry of iPr[Cp-1-Flu]ZrCl$_2$ as prepared in Method B above (6.15 gm, 14 mmol) in methylene chloride (150 ml) at $-78°$ C. The cold bath was removed from the flask and stirring was continued for 1 hour after being warmed to room temperature. The solvents were removed in vaccum and the yellow residue was extracted with a toluene/pentane mixture (50/50, 150 ml), concentration to 10 ml and cooling to 0° C. gave 1.4 gm of yellow iPr[Cp-1-Flu[Zr(CH$_3$)$_2$. The complex was filtered and washed with two 10 ml portion of cold pentane. An additional 2.0 gm of iPr[Cp-1-Flu[Zr(CH$_3$)$_2$ was extracted from the MgCl$_2$ mixture with 100 ml of toluene; leaving 6.7 gm of an insoluble white powder; assumed to be MgCl$_2$.2THF. The yield was 62% based on Zr. 1H NMR (CD2C12, at 5.32 ppm): d(2H) 8.14; d(2H) 7.67; t(2H) 7.36; t(2H) 6.25; d(2H) 5.55; S(6H) 2.09; 8(6H) $-1.63$.

As noted previously, a preferred mode of converting the neutral metallocenes to cationic metallocene catalyst useful in the present invention involves reaction of the neutral metallocenes with a triphenylcarbenium boronate. A preferred reactant is tripheylcarbenium tetrakis (pentafluorphenyl) boronate. The following examples illustrate various bridged cationic metallocene catalysts used in producing polypropylene in accordance with the invention.

EXAMPLE 1

120 mg of triphenylcarbenium tetrakis (pentafluorophenyl)boronate was dissolved in 10–20 ml of toluene. 80 mg of isopropylidene(cyclopentadienyl-1-fluorenyl)zirconium dimethyl, abbreviated iPr(Cp-1-Flu)ZrMe$_2$, was dissolved in 10–20 ml of toluene. The two solutions were mixed together for 5 minutes at room temperature.

The reactor temperature was set at 70° C. and one liter of propylene was pumped into the reactor. The catalyst mixture was added to a 50 ml stainless steel bomb. 200 ml of propylene was pumped through the bomb into the reactor. The contents of the reactor were agitated for ten minutes. Reactor temperature increased to over 100° C. Unreacted propylene was vented from the reactor.

The reaction product was washed with acetone and dried in a vacuum. The polymer was weighed and analyzed for melting point. The melting point was derived from differential scanning calorimetry (DSC).

EXAMPLE 2

The procedure of Example 1 was reported using 60 mg of triphenylcarbenium tetrakis(pentafluorophenyl)boronate, 40 mg of isopropylidene(cyclopentadienyl-1-fluorenyl)zirconium dimethyl, and a run time of sixty minutes.

EXAMPLE 3

The procedure of Example 1 was repeated using 60 mg of triphenylcarbenium tetrakis(pentafluorophenyl)boronate, 40 mg of isopropylidene(cyclopentadienyl-1-fluorenyl)zirconium dimethyl, a reactor temperature of 80° C. and a run time of sixty minutes.

EXAMPLE 4

The procedure of Example 1 was repeated using 100 mg of triphenylcarbenium tetrakis(pentafluorophenyl)boronate and 60 mg of iPr(Cp-1-Flu)ZrMe$_2$. The reactor temperature was set at 70° C. The contents of the reactor were agitated for one hour. The results are shown in Table I.

EXAMPLE 5

0.16 mmol of trimethylaluminum (TMA) was dissolved in 2 ml of toluene and added to a Zipperclave reactor. The reactor temperature was set to 70° C. and 1.5 liter of propylene was added to the reactor. The mixture was stired for 10 minutes at 1200 rpm.

100 mg of triphenylcarbenium tetrakis (pentafluorophenyl)boronate was dissolved in 10-20 ml of toluene. 60 mg of iPr(Cp-1-Flu)ZrMe$_2$ was dissolved in 10-20 ml of toluene. The two solutions were mixed together for five minutes at room temperature.

The catalyst mixture was added to a 50 ml stainless steel bomb. 200 ml of propylene was pumped through the bomb into the reactor. The contents of the reactor were agitated for one hour. Unreacted propylene was vented from the reactor.

The reaction product was washed with acetone and dried in a vacuum. The polymer was weighed and analyzed for melting point. The melting point was derived from differential scanning calorimetry (DSC). The results are shown in Table I.

EXAMPLE 6

The procedure of Example 5 was repeated using 0.48 mmol of trimethylaluminum (TMA), 100 mg of triphenylcarbenium tetrakis(pentafluorophenyl)boronate and 60 mg of iPr(Cp-1-Flu)ZrMe$_2$. The contents of the reactor were agitated for one hour. The results are shown in Table I.

EXAMPLE 7

The procedure of Example 5 was repeated using 0.16 mmol of trimethylaluminum (TMA), 60 mg of triphenylcarbenium tetrakis(pentafluorophenyl)boronate and 20 mg of iPr(Cp-Flu)ZrMe$_2$. The contents of the reactor were agitated for one hour. The results are shown in Table I.

EXAMPLE 8

0.16 mmol of trimethylaluminum (TMA) was dissolved in 2 ml of toluene and added to a Zipperclave reactor. The reactor temperature was set to 70° C. and 1.5 liter of propylene was added to the reactor. The mixture was stirred for 10 minutes at 1200 rpm.

46 mg of tris(pentafluorophenyl) boron was dissolved in 10-20 ml of toluene. 35 mg of iPr(Cp-1-Flu)ZrMe$_2$ was dissolved in 10-20 ml of toluene. The two solutions were mixed together for 5 minutes at room temperature.

The catalyst mixture was added to a 50 ml stainless steel bomb. 200 ml of propylene was pumped through the bomb into the reactor. The reactor temperature increased to 75° C. and the contents of the reactor were agitated for 30 minutes. Unreacted propylene was vented from the reactor.

The reaction production was washed with acetone and dried in a vacuum. The polymer was weighed and analyzed for melting point. The melting point was derived from differential scanning calorimetry (DSC). The results are shown in Table I.

EXAMPLE 9

The procedure of Example 8 was repeated using 0.33 mmol of triethylaluminum (TEA1), 78.6 mg of tris(pentafluorophenyl) boron and 60 mg of iPr(Cp-1-Flu)ZrMe$_2$. The contents of the reactor were agitated for 30 minutes. The results are shown in Table I.

EXAMPLE 10

The procedure of Example 8 was repeated using 0.33 mmol of triethylaluminum (TEA1), 27 mg of tris(pentafluorophenyl) boron and 20 mg of iPr(Cp-1-Flu)ZrMe$_2$. The contents of the reactor were agitated for 30 minutes. The results are shown in Table I.

EXAMPLE 11

The procedure of Example 8 was repeated using 0.33 mmol of triethylaluminum (TEA1), 46 mg of tris(pentafluorophenyl) boron and 35 mg of iPr(Cp-1-Flu)ZrMe$_2$. The contents of the reactor were agitated for 30 minutes. The results are shown in Table I.

EXAMPLE 12

The procedure of Example 8 was repeated using 0.16 mmol of triethylaluminum (TEA1), 46 mg of tris(pentafluorophenyl) boron and 35 mg of iPr(Cp-1-Flu)ZrMe$_2$. The contents of the reactor were agitated for 30 minutes. The results are shown in Table I.

EXAMPLE 13

The procedure of Example 8 was repeated using 0.10 mmol of triethylaluminum (TEA1), 46 mg of tris(pentafluorophenyl)boron and 35 mg of iPr(Cp-1-Flu)ZrMe$_2$. The contents of the reactor were agitated for 30 minutes. The results are shown in Table I.

EXAMPLE 14

The procedure of Example 8 was repeated using 0.16 mmol of triethylaluminum (TEA1), 46 mg of tris(pentafluorophenyl)boron and 15 mg of iPr(Cp-1-Flu)ZrMe$_2$. The contents of the reactor were agitated for 30 minutes. The results are shown in Table I.

TABLE I

| | iPr(Cp-1-Flu)ZrMe$_2$ umol (mg) | umol (mg) | Aluminum Alkyl mmol | Run Time min. | Polymerization Temp °C. | Yield gms | Melting Temp °C. |
|---|---|---|---|---|---|---|---|
| | | [Ph$_3$C][BPh*$_4$] | | | | | |
| 1. | 204 (80) | 130 (120) | 0 | 5 | 70 | 224 | 115 |
| 2. | 102 (40) | 65 (60) | 0 | 60 | 70 | 186 | 119 |
| 3. | 102 (40) | 65 (60) | 0 | 60 | 80 | 2 | 80 |
| 4. | 154 (60) | 109 (100) | 0 | 60 | 70 | 51 | — |
| 5. | 154 (60) | 109 (100) | TMA 0.16 | 60 | 70 | 284 | 116 |
| 6. | 154 (60) | 109 (100) | 0.48 | 60 | 70 | 268 | 117 |
| 7. | 51 (20) | 65 (60) | 0.16 | 60 | 70 | 156 | 116 |
| | | B(C$_6$F$_5$)$_3$ | | | | | |
| 8. | 89.5 (35) | 89.8 (46) | TMA 0.16 | 30 | 70 | 167 | |
| 9. | 153 (60) | 153 (78.6) | TEA1 0.33 | 30 | 70 | 123 | |
| 10. | 51.2 (20) | 52.73 (27) | 0.33 | 30 | 70 | 7 | 110 |
| 11. | 89.5 (35) | 89.8 (46) | 0.33 | 30 | 70 | 110 | 123 |
| 12. | 89.5 (35) | 89.8 (46) | 0.16 | 30 | 70 | 168 | 105 |
| 13. | 89.5 (35) | 89.8 (46) | 0.10 | 30 | 70 | 5 | 105 |

TABLE I-continued

| iPr(Cp-1-Flu)ZrMe$_2$ umol (mg) | | umol (mg) | Aluminum Alkyl mmol | Run Time min. | Polymerization Temp °C. | Yield gms | Melting Temp °C. |
| --- | --- | --- | --- | --- | --- | --- | --- |
| 14. | 38.4 (15) | 89.8 (46) | 0.16 | 30 | 70 | 58 | |

I claim:

1. A metallocene catalyst for use in the syndiotactic propagation of a polymer chain comprising an unbalanced metallocene cation and a stable noncoordinating anion for said metallocene cation characterized by the formula:

$$[R''(CpR_n)(CpR'_m)MeQ_k]^+ [P^-_a]$$

wherein:
each Cp is a cyclopentadienyl ring;
each R is the same or different and is a hydrocarbyl radical having 1–20 carbon atoms;
each R' is the same or different and is a hydrocarbyl radical having 1–20 carbon atoms and is selected such that (CpR'm) is sterically different ring than (CpRn);
R" is a structural bridge between the Cp rings imparting stereorigidity to the catalyst;
Me is a group 4b, 5b or 6b metal from the Periodic Table of Elements;
each Q is a hydrocarbyl radical having 1–20 carbon atoms or is a halogen;
$P_a$ is a stable noncoordinating anion;
n is from 0 to 4, m is from 1 to 4, and k is from 0 to 2.

2. The catalyst of claim 1 wherein Me is titanium, zirconium or hafnium and K is 1.

3. The catalyst of claim 1 wherein R'$_m$ is selected such that (CpR'$_m$) forms a fluorenyl or indenyl radical.

4. The catalyst of claim 1 wherein R" is selected from the group consisting of an alkylene radical having 1–4 carbon atoms, a silicon hydrocarbyl radical, a germanium hydrocarbyl radical, a phosphorus hydrocarby radical, a nitrogen hydrocarbyl radical, a boron hydrocarbyl radical, and an aluminum hydrocarbyl radical.

5. The catalyst of claim 2 wherein R" is a methyl, ethyl, isopropyl, cyclopropyl, dimethylsilyl, methylene or ethylene radical.

6. The catalyst of claim 5 wherein Q is a methyl group.

7. The process of claim 6 wherein R'$_m$ is selected such that (CpR'm) forms a fluorenyl or indenyl radical.

8. The catalyst of claim 1 wherein R"(CpRn)(CpR'm) forms an isopropylidone (cyclopentadienyl-1-fluorenyl) radical.

* * * * *

UNITED STATES PATENT AND TRADEMARK OFFICE
CERTIFICATE OF CORRECTION

PATENT NO. : 5,155,080
DATED : October 13, 1992
INVENTOR(S) : Michael J. Elder, Abbas Razavi, John A. Ewen It is certified that error appears in the above-identified patent and that said Letters Patent is hereby corrected as shown below:

On title page, item [63]
    Related U.S. Application Data
      Continuation-in-part of Ser. No. 220,007, July 15, 1988,
      Pat. No. 4,892,851

Signed and Sealed this

Seventh Day of September, 1999

Attest:

Q. TODD DICKINSON

*Attesting Officer*     Acting Commissioner of Patents and Trademarks